United States Patent [19]

Malchesky et al.

[11] Patent Number: 5,407,685
[45] Date of Patent: Apr. 18, 1995

[54] CONTROLLED OXYGEN/ANTI-MICROBIAL RELEASE FILMS

[75] Inventors: Paul S. Malchesky, Painesville Township, Lake County; Raymond C. Kralovic, Ashtabula, both of Ohio

[73] Assignee: Steris Corporation, Mentor, Ohio

[21] Appl. No.: 64,391

[22] Filed: May 18, 1993

Related U.S. Application Data

[63] Continuation-in-part of Ser. No. 23,048, Feb. 25, 1993, which is a continuation-in-part of Ser. No. 793,589, Nov. 18, 1991, Pat. No. 5,209,909, which is a continuation-in-part of Ser. No. 681,118, Apr. 5, 1991, Pat. No. 5,217,698, and Ser. No. 342,189, Apr. 24, 1989, Pat. No. 5,116,575, said Ser. No. 681,118, is a continuation-in-part of Ser. No. 349,304, May 9, 1989, Pat. No. 5,091,343, and Ser. No. 342,189, Apr. 24, 1989, said Ser. No. 349,304, is a continuation-in-part of Ser. No. 140,388, Jan. 4, 1988, Pat. No. 4,892,706, said Ser. No. 342,189, is a continuation-in-part of Ser. No. 229,917, Aug. 8, 1988, Pat. No. 5,077,008, which is a continuation-in-part of Ser. No. 140,388, Aug. 8, 1988, and Ser. No. 165,189, Mar. 17, 1988, Pat. No. 5,037,623, said Ser. No. 140,388, and Ser. No. 165,189, each is a continuation-in-part of Ser. No. 826,730, Feb. 6, 1986, Pat. No. 4,731,222.

[51] Int. Cl.⁶ .............................................. A61F 13/00
[52] U.S. Cl. .................................. 424/449; 424/402; 424/404; 424/443; 424/446; 424/448; 424/660; 206/361; 2/16
[58] Field of Search ............... 424/449, 404, 438, 448, 424/660, 443, 402

[56] References Cited

U.S. PATENT DOCUMENTS 4,008,351 2/1977 Inoue et al. .......................... 428/411

(List continued on next page.)

FOREIGN PATENT DOCUMENTS

| | | |
|---|---|---|
| 351907A2 | 6/1989 | European Pat. Off. . |
| 332310A2 | 9/1989 | European Pat. Off. . |
| 365160A2 | 4/1990 | European Pat. Off. . |
| 395296A2 | 10/1990 | European Pat. Off. . |
| 507461A2 | 10/1992 | European Pat. Off. . |
| 89/05093 | 6/1989 | WIPO . |
| 92/19287 | 11/1992 | WIPO . |

OTHER PUBLICATIONS

"Desinfectant Effect of Persteril In Combination With Detergents/", V. Melicherčíková, Journal of Hygiene, Epidermilogy, Microbiology and Immunology, 33, 1989, No. 1, 19–28.

(List continued on next page.)

Attorney, Agent, or Firm—Fay, Sharpe, Beall, Fagan, Minnich & McKee

[57] ABSTRACT

A film for releasing at least one of an anti-microbial agent, oxygen, and a medicament includes a flexible, porous layer (18) such as a woven, non-woven, or knitted cloth or a layer of open cell foam. A first dry reagent (12) and a second dry reagent (14) which react in the presence of a dilutant to form the anti-microbial agent, oxygen, or medicament attached to the flexible, porous layer. In one preferred embodiment, the two dry reagents are disposed on opposite sides of the flexible, porous layer such that the flexible porous layer keeps the two apart and prevents a premature reaction. Porous outer layers (20, 22) prevent the powdered reagents from being wiped off while permitting dilutant access. In a preferred embodiment, the powdered reagents include acetylsalicylic acid and a perborate which react in the presence of water to generate peracetic acid (an antimicrobial agent which breaks down in a matter of minutes to hours into oxygen) and salicylic acid (a topical keratotic). The rate at which the reaction occurs and the peracetic acid breaks down into oxygen is controlled by buffering the pH of the powdered reagents, by selectively micro-encapsulating the powdered reagents, by controlling the porosity of the layers, or the like. Optionally, surfactants, detergents, emollients, gels, and the like can be added to the dry reagents. Alternately, a single reagent which releases oxygen or forms a strong oxidant may be used.

29 Claims, 3 Drawing Sheets

U.S. PATENT DOCUMENTS

| | | | |
|---|---|---|---|
| 4,228,149 | 10/1980 | Brewer | 424/14 |
| 4,268,497 | 5/1981 | Griffin | 424/438 |
| 4,272,264 | 6/1981 | Cullen et al. | 55/387 |
| 4,405,347 | 9/1983 | Cullen et al. | 55/387 |
| 4,453,955 | 6/1984 | Cullen et al. | 55/387 |
| 4,457,843 | 7/1984 | Cullen et al. | 210/282 |
| 4,505,727 | 3/1985 | Cullen et al. | 55/387 |
| 4,584,192 | 4/1986 | Dell et al. | 424/81 |
| 4,601,893 | 7/1986 | Cardinal | 424/438 |
| 4,619,673 | 10/1986 | Cullen et al. | 55/337 |
| 4,687,481 | 8/1987 | Nuwayser | 424/449 |
| 4,728,323 | 3/1988 | Matson | 604/304 |
| 4,749,600 | 6/1988 | Cullen et al. | 428/35 |
| 4,756,710 | 7/1988 | Bondi | 424/449 |
| 4,783,206 | 11/1988 | Cullen et al. | 55/387 |
| 4,847,089 | 7/1989 | Kramer et al. | 424/405 |
| 4,877,816 | 10/1989 | Murabayashi et al. | 521/92 |
| 4,990,144 | 2/1991 | Blott | 604/304 |
| 5,003,638 | 4/1991 | Miyake et al. | 2/167 |
| 5,035,892 | 7/1991 | Blank et al. | 424/443 |
| 5,049,383 | 9/1991 | Huth et al. | 424/405 |
| 5,061,485 | 10/1991 | Oakes et al. | 424/81 |
| 5,069,907 | 12/1991 | Mixon et al. | 424/445 |
| 5,079,004 | 1/1992 | Blank et al. | 424/404 |
| 5,091,102 | 2/1992 | Sheridan | 252/91 |
| 5,092,914 | 3/1992 | Cullen et al. | 55/316 |
| 5,104,660 | 4/1992 | Chvapil et al. | 424/445 |
| 5,108,740 | 4/1992 | Greenwald et al. | 424/78 |
| 5,142,010 | 8/1992 | Olstein | 526/248 |
| 5,154,920 | 10/1992 | Flesher et al. | 514/643 |
| 5,178,495 | 1/1993 | Cameron | 405/303 |
| 5,209,909 | 5/1993 | Siegel et al. | 424/292 |

OTHER PUBLICATIONS

"Studies Concerning the Mechanism of Bleaching Activation", Hauthal, et al. Tenside Surf. Det. 27 (1990) 3, pp. 187–193.

"Effect of pH on Sproicidal and Microbicidal Activity of Buffered Mixtures of Alcohol and Sodium Hypochlorite", Death, et al., J. of Clinic Pathology 1979, 32 148–153.

*Primary Examiner*—D. Gabrielle Phelan

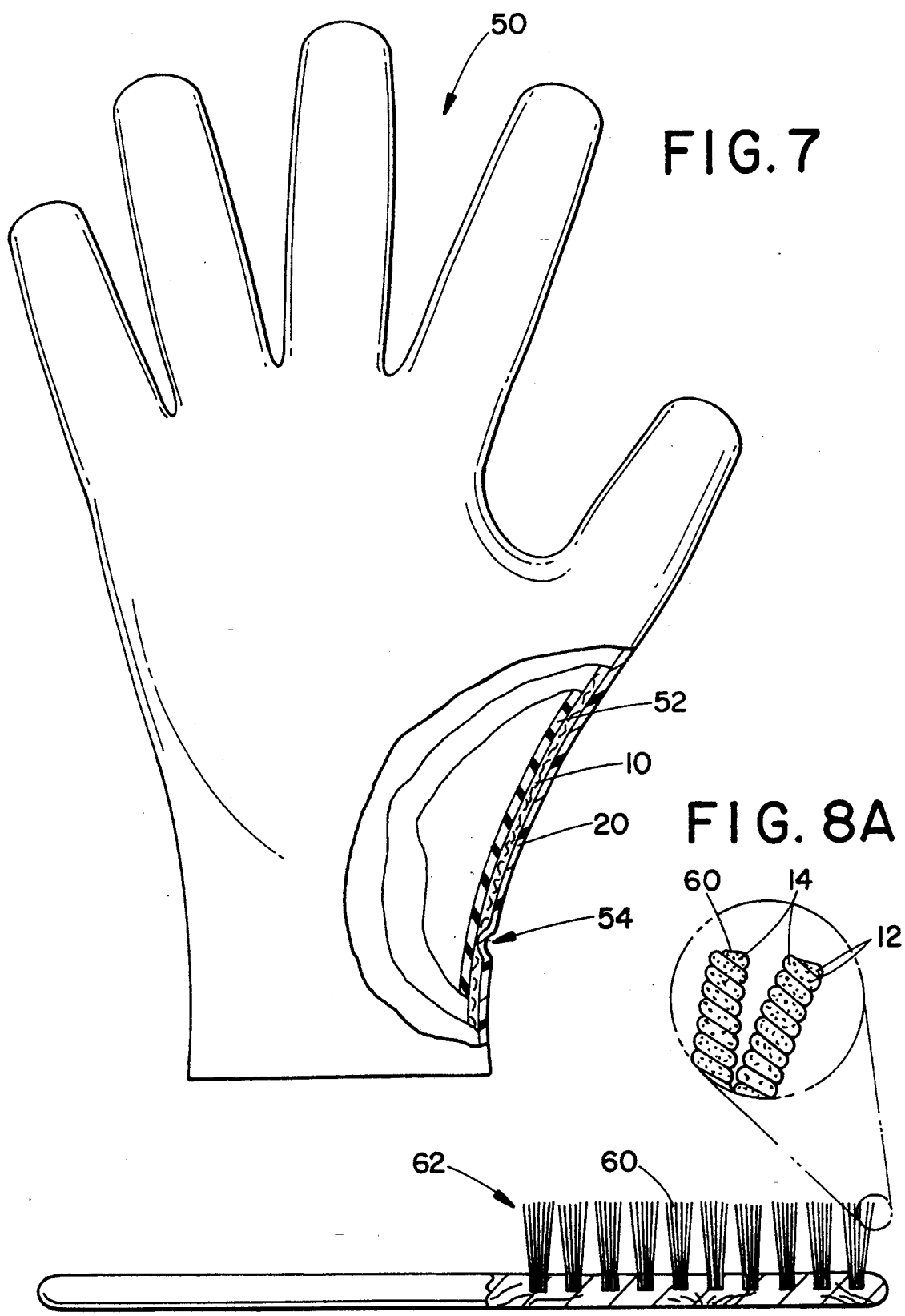

CONTROLLED OXYGEN/ANTI-MICROBIAL RELEASE FILMS

This application is a continuation-in-part of U.S. application Ser. No. 08/023,048, filed Feb. 25, 1993 which is a continuation-in-part of U.S. application Ser. No. 07/793,589, filed Nov. 18, 1991, now U.S. Pat. No. 5,209,909, which is a continuation-in-part of U.S. application Ser. No. 07/681,118, filed Apr. 5, 1991, now U.S. Pat. No. 5,217,698 and U.S. application Ser. No. 07/342,189, filed Apr. 24, 1989, now U.S. Pat. No. 5,116,575.

U.S. application Ser. No. 07/681,118, is a continuation-in-part of U.S. application Ser. No. 07/349,304, filed May 9, 1989, now U.S. Pat. No. 5,091,343, and said U.S. application Ser. No. 07/342,189. U.S. application Ser. No. 07/349,304 is a continuation-in-part of U.S. application Ser. No. 140,388, filed Jan. 4, 1988, now U.S. Pat. No. 4,892,706. U.S. application Ser. No. 07/342,189 is a continuation-in-part of U.S. application Ser. No. 229,917, filed Aug. 8, 1988, now U.S. Pat. No. 5,077,008, which is a continuation-in-part of said U.S. application Ser. No. 140,388 and U.S. application Ser. No. 07/165,189, now U.S. Pat. No. 5,037,623, filed Mar. 17, 1988, which in turn are continuations-in-part of U.S. application Ser. No. 826,730, filed Feb. 6, 1986, now U.S. Pat. No. 4,731,222.

BACKGROUND OF THE INVENTION

The present invention relates to the microbial decontamination arts. It finds particular application with bandages and wipes and will be described with particular reference thereto. It is to be appreciated, however, that the present invention will also find application in other areas where oxidants, anti-microbial agents, or medicaments are generated in situ such as in gloves, drapes, and the like.

Heretofore, various wipes and other cloth-like materials have been impregnated with an anti-microbial agent. The anti-microbial agent, most often in a liquid form, is coated on, caused to soak into, or otherwise attached to a flexible carrier or film. Often, the antimicrobial agent treated film is packaged in a sealed pouch to prevent evaporation or contamination. The pouch is opened to use the wipe. The wipe is typically packaged with a sufficient amount of a liquid carrier that a wet layer of carrier and anti-microbial agent are left on the wiped surface. Alternately, the carrier or a dilutant such as water may be added to the film when the package is opened to render the anti-microbial agent more mobile.

Flexible fabric or fiber-like materials which are apt to support mildew, mold, or bacterial growth are often treated with an anti-microbial agent. Often, the fabric or fiber carries materials, e.g., sizing which are apt to support such microbial growth. The anti-microbial agent is typically intermixed with the material which is apt to support microbial growth.

One of the problems with wipes and films of this type is that the anti-microbial agent requires a long shelf life. The wipe may be in the package for weeks or months before it is opened. After the wipe is used and discarded, a significant amount of the anti-microbial agent remains in the wipe. If the anti-microbial agent is a toxin or poison with a long life, disposal of the used wipe carries undesirable environmental and ecological side effects.

The present invention contemplates a new and improved material which overcomes the above-referenced problems and others.

SUMMARY OF THE INVENTION

In accordance with one aspect of the present invention, a film carries one or more constituents which in the presence of a dilutant form oxygen or an anti-microbial agent.

In accordance with a more limited aspect of the present invention, the film is one of a woven, non-woven, or knitted fibers, a flexible foam material, or combinations thereof.

In accordance with another aspect of the present invention, the film carries a single constituent which forms oxygen or an anti-microbial agent.

In accordance with another aspect of the present invention, the film carries at least two constituents that react in the dilutant to form the oxygen or anti-microbial agent. A means is provided to maintain the constituents or reagents separated until contacted with a dilutant.

In accordance with one more limited aspect of the present invention, the two constituents are relatively coarse powders and the means for keeping the two constituents separated includes a filter means which physically blocks the passage of the relatively coarse powders but freely passes the constituents dissolved in the dilutant.

In accordance with another aspect of the present invention, the means for maintaining the constituents separated includes micro-encapsulation of the constituents.

In accordance with yet another aspect of the present invention, the means for maintaining the constituents separated includes immobile implantation of the constituents into the film.

In accordance with another aspect of the present invention, means are provided for controlling a reaction rate between the constituents to control the rate at which the oxygen or anti-microbial agent is produced.

In accordance with a more limited aspect of the present invention, the means for controlling the reaction rate includes added buffers which increase the pH to accelerate the reaction rate or decrease the pH to retard the reaction rate.

In accordance with another aspect of the present invention, the constituents includes a dry or powdered acid precursor and a dry or powdered persalt which react in the dilutant to form an oxidant.

In accordance with a more limited aspect of the present invention, the acid precursor includes an acetyl donor and the persalt includes a perborate. Suitable acetyl donors include acetylsalicylic acid which react with a perborate, preferably sodium perborate monohydrate or sodium perborate anhydrous to form peracetic acid and salicylic acid. The peracetic acid is a strong oxidant which decomposes to liberate free oxygen. The salicylic acid is a keratotic. Other suitable acetyl donors include tetraacetyl ethylenediane (TAED), diactyl dioxohexahydratriazine (DADHT), tetraacetyl glycoluril, and sodium nanonoyl oxygenzene sulfonate. Optionally, emollients and other therapeutically beneficial constituents may also be added.

In accordance with another aspect of the present invention, the constituents are micro-encapsulated and the means for controlling the reaction rate includes controlling the micro-encapsulation such that the dilutant dissolves the micro-encapsulation relatively quickly on all particles for a more rapid reaction rate and dissolves a larger fraction of the particles more slowly for a slow reaction rate.

In accordance with another more limited aspect of the present invention, a film of limited permeability is provided for limiting movement of the dilutant to the constituents.

In accordance with another aspect of the present invention, the powdered constituents include a perborate for generating oxygen and oxidants.

In one method of use, the film material is formulated such that the constituents react quickly, i.e. have a very short half-life. The film or the surface to be disinfected are wet, such as by spraying or dipping. The dilutant allows the constituents to react, generating the anti-microbial agent or oxidant. Preferably, the half-life of the anti-microbial agent or oxidant is only a minute or two.

In accordance with another aspect of the present invention, the film is incorporated in a bandage and configured such that the reaction progresses very slowly, i.e. there is a long half-life. The bandage is placed over a wound. Moisture from the wound acts as the dilutant allowing the reaction which produces the anti-microbial agent and/or oxidant to take place. Preferably, the half-life is on the order of several hours to a day or two such that the anti-microbial agent or oxygen is produced substantially continuously over the time that the dressing is applied to the wound. Optionally, the constituents may be configured to give a high initial concentration for disinfection and a slow continuing oxygen release.

In accordance with another aspect of the present invention, the film is incorporated into a glove. The glove is constructed with an impermeable inner layer adjacent the wearer's hand and the film is affixed to the exterior. The glove is wet with a dilutant such that the anti-microbial agent or strong oxidant is produced on its surface. The impermeable inner lining of the glove prevents the anti-microbial agent or strong oxidant from reaching the hand of the wearer.

One advantage of the present invention is that it has a relatively long shelf-life and a relatively short half-life.

Another advantage of the present invention is that the anti-microbial agent or oxidant is generated in situ at a controllable rate.

Another advantage of the present invention is that it effectively kills microbes yet is not polluting when discarded.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 7 illustrates a glove incorporating the present invention; and,

FIGS. 8 and 8A illustrate a brush incorporating the present invention.

DETAILED DESCRIPTION OF THE PREFERRED EMBODIMENTS

Figure 1:
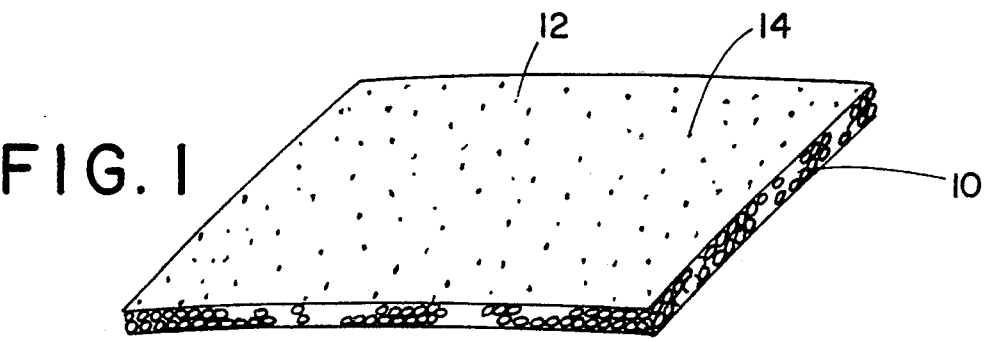
FIG. 1 illustrates a film impregnated with dry reagents which react in the presence of a dilutant to form an anti-microbial agent or oxidant.

With reference to FIG. 1, a film 10 is impregnated with a first reagent or constituent 12 and a second reagent or constituent 14, which reagents react in situ in the presence of a dilutant to form an antimicrobial agent, a strong oxidant, or oxygen. In one preferred embodiment, one of the reagents 12 includes a sodium or other perborate in dry form or other dry constituents which liberate oxygen. Sodium perborate monohydrate and sodium perborate anhydrous are preferred. The other reagent 14 includes a dry acid precursor. The dry acid precursor and the dry persalt react when dissolved in water or other appropriate dilutants to form a strong oxidant. Further to the preferred embodiment, the acid precursor is an acetyl donor, such as acetylsalicylic acid, tetraacetyl ethylenediane (TAED), diactyl dioxohexahydratriazine (DADHT), tetraacetyl glycoluril, and sodium nanonoyl oxygenzene sulfonate. Acetylsalicylic acid and sodium perborate react in water to form peracetic acid, salicylic acid, and sodium metaborate. Peracetic acid is a strong oxidant with a relatively short half-life that liberates free oxygen as it breaks down. Salicylic acid is a topical keratotic which softens or dissolves horny layers of the epidermis such as warts, callouses, and dead skin. In addition to softening skin, salicylic acid has anti-microbial properties.

Single constituent systems which react in a solvent, such as water, to release oxygen are also contemplated. Preferred single constituents include stable solid acetyl peroxyborate, magnesium monoperoxy phthalate, and urea peroxide.

In use, the film 10, an open cell foam in the embodiment of FIG. 1, is brought into contact with water or other dilutant such that the physically displaced implanted dry acid precursor and dry persalt or the single constituent are dissolved and react forming an antimicrobial agent and liberating oxygen. When used as a wipe, the film may be dipped or sprayed with water to activate it. Alternately, the surface to be disinfected may be wet such that the film and the impregnated reagents become wet, dissolve, and react from the water on the surface. When used as a bandage, the film may be initially dampened, such as with spray, to start the reaction. The reaction may be continued or in some embodiments initiated by moisture from the wound. When used as a dressing, the oxidant disinfectant agent not only functions as an anti-microbial agent to prevent infection, but also liberates free oxygen which promotes healing.

Figure 2:
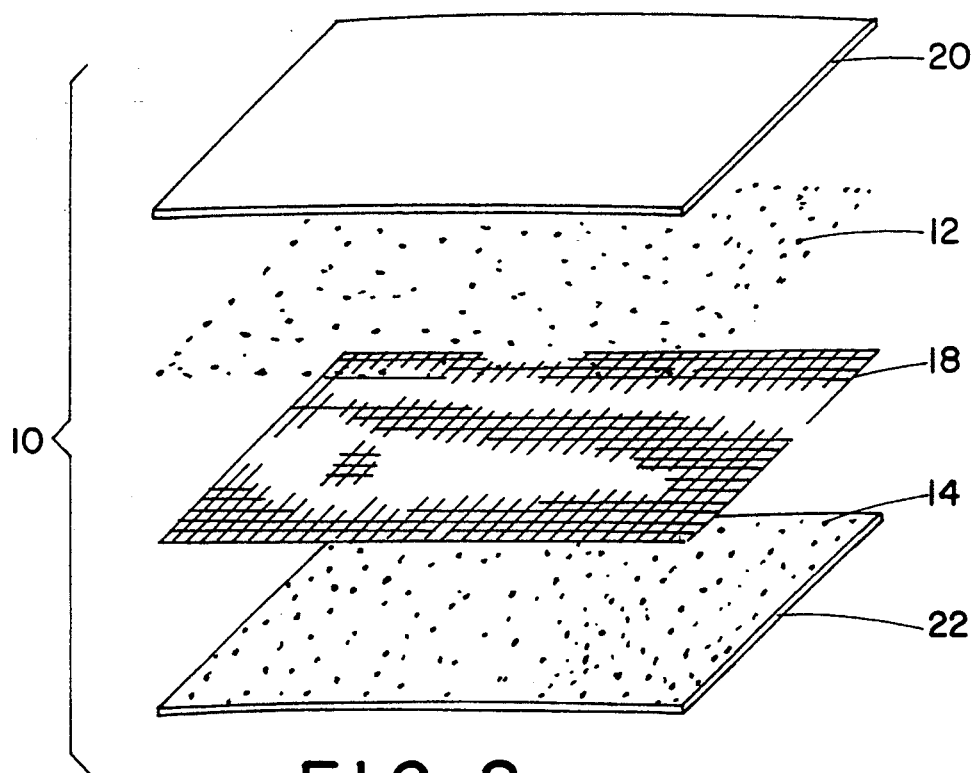
FIG. 2 illustrates another embodiment of the present invention in which reagent particles are separated by a filter.

With reference to FIG. 2, rather than implant the dry constituents or reagents 12, 14 physically displaced from each other, other means can be provided for maintaining the dry constituents separated until activated by the dilutant. In the embodiment of FIG. 2, particles of the first reagent 12 and particles of the second reagent 14 are separated by a filter sheet 18. The filter sheet has a pore size which is sufficiently small relative to a particle size of the two powdered reagents that the particles are maintained physically separated. Yet, once dissolved in the dilutant, the pore size is sufficiently large that the dilutant and dissolved materials pass therethrough and react. A top or first outside coating layer 20 and a bottom or second outside coating layer 22 shield the particles of the two reagents from physical interaction so that they are not lost or brushed off before the film is actuated with the dilutant. At least one of the two covering layers is permeable to the dilutant to allow ready access to the constituents.

It is also advantageous to control the reaction rate such that the rate at which the anti-microbial agent or oxygen is produced occurs substantially at a preselected rate. In the embodiment of FIG. 2, a means for controlling the reaction includes the pore size of the filter material 18. In one embodiment, the reaction rate is controlled by limiting communication between the constituents. The means for controlling the reaction rate further includes the permeability of the covering layers 20 and 22. By limiting the rate at which the dilutant can reach the dry constituents, the rate at which there is sufficient dilutant to allow them to react is controllable. In another embodiment, the means for controlling the reaction rate includes the addition of further powdered reagents. In particular, the reaction between the preferred acetylsalicylic acid and sodium perborate is pH sensitive. At a high pH, the reaction occurs quickly. When the pH is buffered such that it remains near neutral even when the peracetic acid is produced, the reaction proceeds more slowly. The peracetic acid buffered nearer neutral remains stable for a relatively long duration, generally on the order of hours, rather than breaking down into oxygen quickly as it does when the pH is high. Lower pH serves as a stabilizer. Analogously, temperature affects the reaction. The maximum yields of peracetic acid are higher at 20° C. while the times needed to reach the maximum are longer at lower temperature. The time for converting TAED to peracetic acid is longer than for DADHT.

Figure 3:
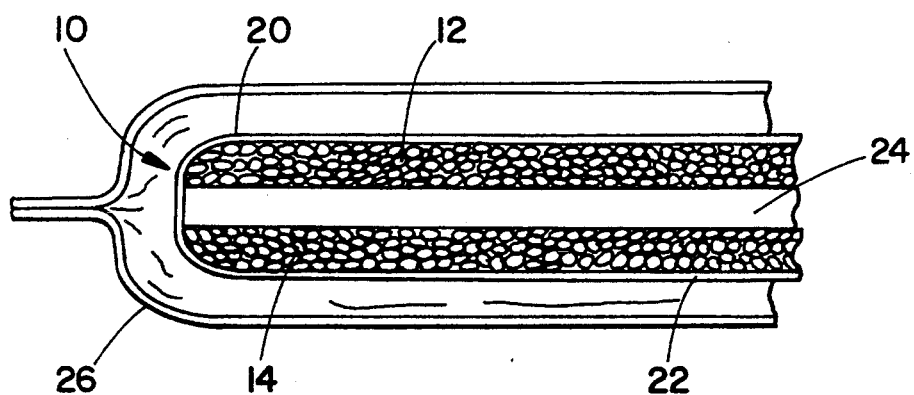
FIG. 3 illustrates another embodiment of the present invention incorporated into a wipe.

With reference to FIG. 3, the film 10 includes readily porous upper and lower layers 20, 22 between which the powdered reagents are contained. A dry, moisture absorbing gel material 24, such as sodium silicate, separates the dry first reagent 12 and second reagent 14. The dry gel 24 absorbs moisture strongly forming a wet slush which permits the powdered constituents 12 and 14 to mix and react. A hermetic seal, such as a plastic or cellophane package or a foiled pouch 26 encompasses and seals the film 10 to prevent moisture from being absorbed by the gel and starting the reaction prematurely. The gel may be formulated chemically or configured physically, such as by the addition of a porous fabric layer, to control the rate at which the dry reagents are dissolved and intermix to react. Further, the dry reagents may again be encapsulated to control the reaction rate. pH buffers or other reaction controlling constituents are preferably physically intermixed with either the first or the second powdered reagent or the gel. The dry reagents of the wipe may also include surfactants or wetting agents, detergents, moisture-absorbing gels to remove water from the wiped surface, and the like.

Figure 4:
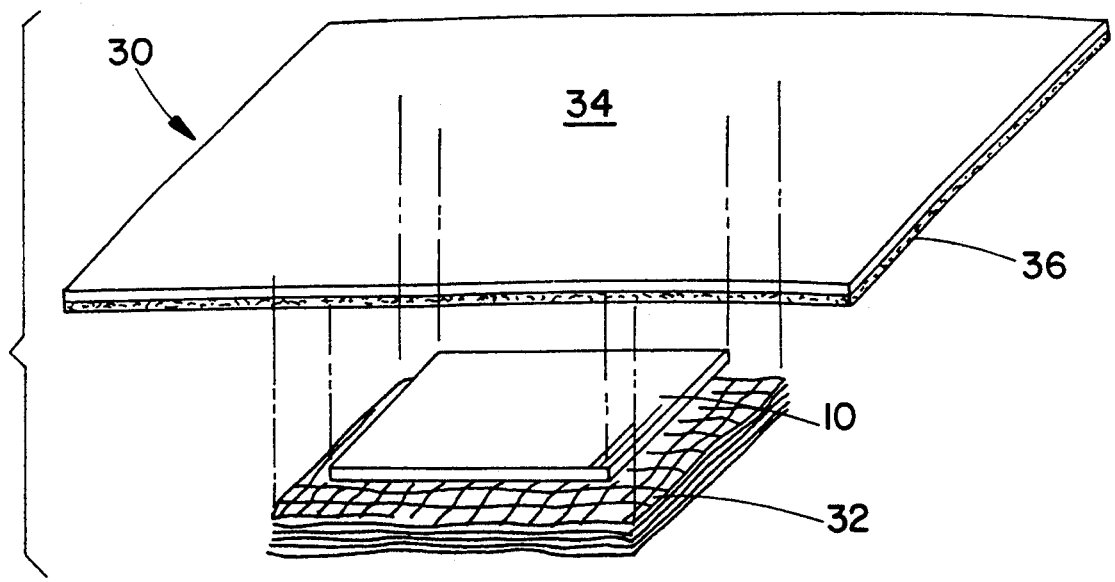
FIG. 4 illustrates a wound dressing in accordance with the present invention.

With reference to FIG. 4, a wound dressing includes a section of the film 10 disposed between a gauze or other porous wound contacting layer 32 and a covering layer 34. Preferably, the covering layer 34 includes an adhesive layer 36 which adheres to the film 10 to a central portion thereof, adheres the wound contacting portion 32, and adheres to the patient's skin around the wound. The film 10 may have the construction set forth in any of the preceding FIGURES or in those described below. In one preferred embodiment, the film 10 has substantially the construction of FIG. 2. The lower layer 22 disposed towards the patient's skin is porous to moisture exiting the wound. Lower layers of different porosity are used for different types of wounds. For example, the bandage is advantageously used to generate oxygen to promote the healing of a wound. The lower layer 22 has a porosity which permits water vapor to pass therethrough at a controlled rate. The water vapor causes a limited wetting of the dry reagents such that they dissolve gradually and react, at an analogous controlled rate. Preferably, the powdered constituents are buffered to have a relatively high pH such that the preferred acetylsalicylic acid and perborate form a peracetic acid with such a high pH that it is relatively unstable and breaks down quickly to free oxygen. A pH of 11 or higher is preferred for a quick breakdown to oxygen. The porosity of the lower layer 22 is again permeable to the free oxygen such that it enters the wound. The upper layer 20, being redundant with the layer 34 may be eliminated. The layer 34, and layer 20 if redundantly applied, may be moisture and gas permeable or may be semipermeable to either moisture or gas. Venting allows excess water vapor to escape. In some applications, layer 34 is impermeable.

For other types of wounds, the generation of a strong anti-microbial agent is important as well as the production of oxygen. The porosity of lower layer 22 is again selected to control the amount of moisture permitted to enter. If the dressing is to be applied for a relatively short duration, e.g. a few hours, the lower layer 22 is preferably permeable by liquids such as water vapor from the skin, liquids exiting the wounds, or water sprayed from a spray bottle to actuate the dressing.

The preferred acetylsalicylic acid and perborate react to form not only peracetic acid, but also salicylic acid. Preferably, the lower layer 22 is sufficiently porous that it allows the dilutant with dissolved salicylic acid to flow back into the wound to promote healing. As another alternative, the salicylic acid can be used to remove horny layers of the epidermis. The film may be wet, such as by spraying or dipping and then applied to the area to be treated. Preferably, the dry constituents include a gel which holds the water and continues the reaction and permits the salicylic-acid solution to continue to reach the horny layer for several hours to a day. For relatively longer stability, an after reaction pH of 9.2–10 is preferred. The dry reagents 12 and 14 may also include emollients and other skin softeners.

Figure 5:
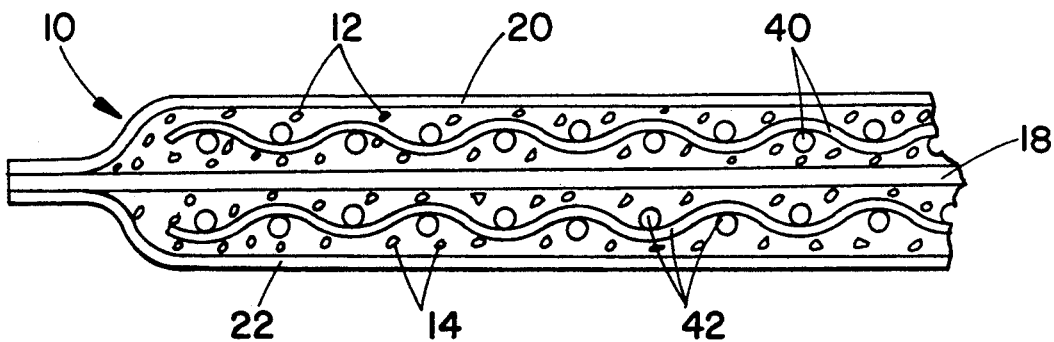
FIG. 5 illustrates another embodiment of the present invention which may advantageously be incorporated into the dressing of FIG. 4.

With reference to FIG. 5, the constituents 12 and 14 are carried by layers of woven, non-woven, or knitted fibers or open cell or foam 40, 42. The dry constituents are sprayed and dried, impregnated, dry sprayed, or otherwise attached to or incorporated into the fibers or foam layers. A filter layer 18 holds the dry particulates apart. Outer layers 20 and 22 contain and protect layers 40 and 42. At least one of the outer layers is fluid permeable such that the dilutant can penetrate, dissolve the dry constituents, and start the chemical reaction. The porosity of the filter 18 and the outer layers 20, 22 control the rate at which the dilutant can enter and the reagents intermix, hence the rate of reaction. Additional buffering compositions may also control the rate of reaction. Surfactants, detergents, emollients, and the like may also be included in dry form.

Figure 6:
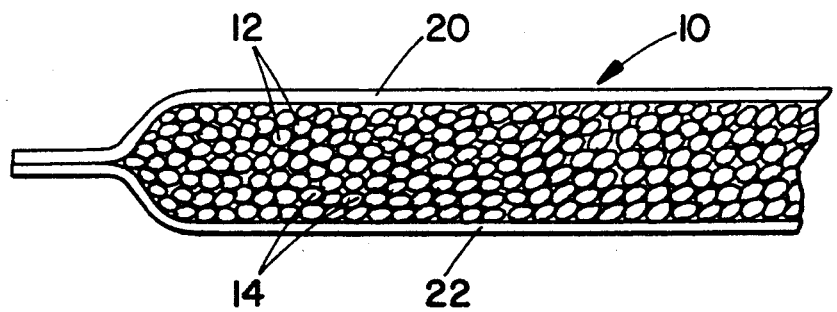
FIG. 6 illustrates yet another embodiment of the present invention in which the reagents are microencapsulated.

In the embodiment of FIG. 6, the single constituent or one or both of the dry reagents 12 and 14 are micro-encapsulated individually. The thickness and the type of the micro-encapsulation controls the reaction rate. For a longer reaction rate, some of the micro-encapsulations are thin to react quickly, others thicker to react more slowly, and others thicker yet such that an extended duration is required before the dilutant penetrates the encapsulation and reaches the dry constituent. The micro-encapsulated constituents or reagents are between outer layers 20, 22. At least one of the outer layers is porous to permit the dilutant to enter and the resultant anti-microbial agent, oxidant, or free oxygen to exit.

With reference to FIG. 7, the constructions of the preceding embodiments can be fabricated into various articles. For example, a protective glove 50 is defined by a continuous impermeable hand-shaped layer 52 of rubber, plastic, or other film material which is impermeable to the dilutant, the anti-microbial agent, strong oxidants, and gaseous oxygen, as well as any emollients, detergents, or other substances which may be dissolved in the dilutant. The film 10 is adhered to the outer surface of all or selected portions of the glove. The film 10 is preferably laminated over the palm, thumb, and finger pad portions of the glove, i.e. the portions of the glove which would contact a grasped or touched object. An outer, permeable layer 22 surrounds the film 10 protecting it. Preferably, the outer layer 22 is a material which can be readily affixed to the impermeable liner 52, such as by heat fusion, adhesives, or the like. Preferably, the film 10 has periodic discontinuities where the inner and outer layers contact and adhere to each other.

With reference to FIGS. 8 and 8A, the single or the plural constituents 12, 14 are impregnated in bristles 60 of a brush 62. The bristles may be natural or synthetic fibers or other constructions which securely hold the dry constituents. When the brush is dipped into a dilutant, the constituents react forming an anti-microbial for scrubbing a surface.

Although the preferred embodiment uses an acetylsalicylic acid and sodium perborate reaction, other oxidizing or antimicrobial agents can also be generated in situ, such as chlorine dioxide, chlorine, hydrogen peroxide, and mixtures thereof. More specifically, potassium chromates, sodium chloride, and phosphates may be mixed according to the following equation to produce a strong chlorine oxidant on the addition of water:

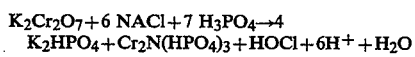
$$K_2Cr_2O_7 + 6\ NACl + 7\ H_3PO_4 \rightarrow 4\ K_2HPO_4 + Cr_2N(HPO_4)_3 + HOCl + 6H^+ + H_2O$$

Optionally, excess dichromate and an organic corrosion inhibitor may be provided for improved buffering and corrosion inhibiting.

Hydrogen peroxide and an inorganic inhibitor can be generated:

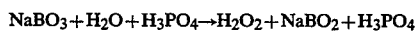
$$NaBO_3 + H_2O + H_3PO_4 \rightarrow H_2O_2 + NaBO_2 + H_3PO_4$$

Similarly, chlorine dioxide can be generated from powdered ingredients on the addition of water:

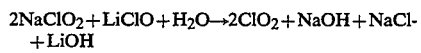
$$2NaClO_2 + LiClO + H_2O \rightarrow 2ClO_2 + NaOH + NaCl + LiOH$$

A mixed biocide system can be achieved by adding sodium chloride to the peracetic acid reaction to produce hypochlorous acid. Because sodium chloride is a component of physiological fluids, the reaction can be partially physiologically regulated.

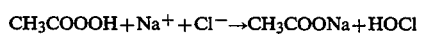
$$CH_3COOOH + Na^+ + Cl^- \rightarrow CH_3COONa + HOCl$$

Excess peracetic acid is deliberately present such that both peracetic acid and hypochlorous acid are present in the biocidal solution.

Other reagents include perborates which react in water to liberate free oxygen, and constituents which react to form other medically useful compositions.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

We claim:

1. A film which releases at least one of an antimicrobial agent and an oxidant, the film comprising:
   a layer of a flexible, porous material;
   a dry persalt comprising a perborate substantially constrained in association with the porous, flexible material layer;
   an acetyl donor of a group consisting of acetylsalicylic acid, tetraacetyl ethylenediane (TAED), diactyl dioxohexahydratriazine (DADHT), tetraacetyl glycoluril, and sodium nanonoyl oxygenzene sulfonate constrained in association with the flexible, porous material layer, the persalt and the acetyl donor reacting in the presence of a dilutant in situ to create a solution containing at least one of the antimicrobial agent and the oxidant.

2. A film which releases at least one of an antimicrobial agent and oxygen, the film comprising:
   a layer of a flexible, porous material;
   a dry perborate substantially constrained in association with the porous, flexible material layer;
   a dry reagent including at least one of a phosphate, acetylsalicylic acid, tetraacetyl ethylenediane (TAED), diactyl dioxohexahydratriazine (DADHT), tetraacetyl glycoluril, and sodium nanonoyl oxygenzene sulfonate constrained in association with the flexible, porous material layer;
   a means for maintaining the perborate and the dry reagent separated in the absence of the dilutant and in the presence of a dilutant, enabling the first and second dry reagents to dissolve and interact generating in situ at least one of the antimicrobial agent solution and oxygen.

3. The film as set forth in claim 2 wherein the means for maintaining the perborate and the dry reagent separated includes at least one of:
   separately encapsulating particles of the perborate and the dry reagent;
   a filter material having pores smaller than a physical size of particles of perborate and the dry reagent for physically separating the particles of the the perborate and the dry reagent;

adhering the perborate to a first flexible layer and adhering the the dry reagent to a second flexible layer, the first and second flexible layers being disposed on opposite sides of the flexible, porous material layer; and impregnating particles of the perborate and dry reagent displaced from each other in the flexible layer.

4. The film as set forth in claim 1 wherein the flexible, porous material includes at least one of:
   woven fibers;
   non-woven fibers;
   knitted fibers;
   a permeable synthetic sheet; and
   a flexible foam layer.

5. The film as set forth in claim 1 further including:
   a first outer layer of a flexible, porous material, the first outer layer being connected with the flexible, porous material with the perborate constrained therebetween; and
   a second outer layer connected with the flexible, porous material layer with the acetyl donor constrained therebetween.

6. A film which releases at least one of an antimicrobial agent and an oxidant, the film comprising:
   an inner layer of a flexible, porous material;
   a first outer layer of a flexible, porous material, the first outer layer being connected on a first side of the inner layer;
   a second outer layer connected on a second side of the inner layer;
   an acetyl donor constrained between the inner layer and the first outer layer; and
   a persalt constrained between the second outer layer and the inner layer, the persalt and the acetyl donor being reactive in the presence of a dilutant to create in situ a solution containing the antimicrobial agent or the oxidant.

7. The film as set forth in claim 1 further including a frangible sealed closure for sealing the flexible film to prevent contact with the dilutant until the sealing enclosure is removed.

8. The film as set forth in claim 1 further including a gauze dressing disposed adjacent one side of the flexible, porous material, the gauze layer being adapted for direct patient contact over a wound or region to be treated; and,
   an adhesive layer for adhering the flexible, porous material layer and the gauze dressing to the patient.

9. The film as set forth in claim 8 wherein the adhesive layer includes a gas impervious layer for preventing released oxygen from escaping to the atmosphere, whereby the released oxygen is channelled through the gauze to the wound or treated patient region.

10. The film as set forth in claim 1 wherein the flexible, porous material layer is connected with an exterior of an impermeable glove.

11. The film as set forth in claim 6 wherein the acetyl donor includes acetylsalicylic acid and the persalt comprises a dry perborate.

12. A film which releases an oxidant, the film comprising:
   a layer of a flexible, porous material;
   a first dry ingredient including at least one of acetylsalicylic acid, tetraacetyl ethylenediane (TAED), diactyl dioxohexahydratriazine (DADHT), tetraacetyl glycoluril, and sodium nanonoyl oxygenzene sulfonate, and phosphate substantially constrained in association with the porous, flexible material layer;
   a second dry reagent including a perborate constrained in association with the porous, flexible material layer, the first dry ingredient and the perborate reacting in the presence of water to generate in situ the oxidant.

13. The film as set forth in claim 1 further including at least one of:
   a surfactant;
   a detergent;
   an emollient;
   a pH buffer; and
   a water absorbing gel constrained in association with the flexible, porous material.

14. A film which releases at least one of an antimicrobial agent and an oxidant, the film comprising:
   a layer of a flexible, porous material;
   a first dry reagent including at least one of acetylsalicylic acid, tetraacetyl ethylenediane (TAED), diactyl dioxohexahydratriazine (DADHT), tetraacetyl glycoluril, sodium nanonoyl oxygenzene sulfonate, and phosphate substantially constrained in association with the porous, flexible material layer;
   a second dry reagent including a perborate constrained in association with the flexible, porous material layer, the first and second reagents being reactive in the presence of a dilutant in situ to create a solution containing at least one of the antimicrobial agent and the oxidant;
   a means for controlling a reaction rate between the first and second reagents.

15. A film which releases at least one of an antimicrobial solution and oxygen, the film comprising:
   a layer of a flexible, porous material;
   a persalt substantially constrained in association with the porous, flexible material layer;
   an acetyl donor comprising at least one of acetylsalicylic acid, tetraacetyl ethylenediane (TAED), diactyl dioxohexahydratriazine (DADHT), tetraacetyl glycoluril, and sodium nanonoyl oxygenzene sulfonate constrained in association with the flexible, porous material layer and separated from the first reagent, the persalt and the acetyl donor being brought together and reacting in the presence of a dilutant to form in situ at least one of the antimicrobial solution and oxygen;
   a means for controlling a rate at which the persalt and the acetyl donor react such that a rate at which the at least one of the antimicrobial solution and oxygen is released is controlled, the reaction rate controlling means including at least one of:
   a porous outer layer which limits a rate of dilutant ingress to the persalt and the acetyl donor;
   micro-encapsulation of at least one of the persalt and the acetyl donor, which micro-encapsulation dissolves at a controllable rate;
   a buffer for buffering a pH during the reaction; and
   a separating filter layer for controlling access of the persalt and the acetyl donor to each other.

16. The film as set forth in claim 14 wherein the means for controlling the reaction rate causes a complete reaction in less than five minutes°

17. An oxidant generating film comprising:
   a natural or synthetic fiber material configured in a porous layer;
   at least one dry constituent held in the fiber material, which dry constituent reacts in a dilutant to generate at least one of oxygen and an oxidant, the dry constituent including at least one of acetylsalicylic acid, tetraacetyl ethylenediane (TAED), diactyl dioxohexahydratriazine (DADHT), tetraacetyl glycoluril, sodium nanonoyl oxygenzene sulfonate, perborate, phosphate, NaClO$_2$, LiClO, a chromate, phosphate, and a chlorine salt.

18. The film as set forth in claim 17 wherein the porous layer is anchored to one end of a paddle member to form a hand holdable scrubber.

19. The film as set forth in claim 17 further including:
a gauze dressing disposed adjacent one side of the porous layer, the gauze dressing being adapted for direct patient contact over a wound to be treated; and
an adhesive layer for adhering the porous layer and gauze dressing to the patient.

20. The film as set forth in claim 17 wherein the at least one dry constituent includes at least two dry components which react with each other in the dilutant to generate the oxidant and oxygen and further including:
a means for maintaining the two dry components separated in the absence of the dilutant.

21. A method of using the film of claim 1, the method comprising:
wetting the film with the dilutant such that the persalt and the acetyl donor dissolve, come together, and react generating the antimicrobial agent solution or the oxidant and bringing the film into contact with a surface to be treated.

22. The method as set forth in claim 21 further including adhering the film to a patient and wherein the wetting step includes wetting the film with moisture emitted from the patient such that moisture from the patient causes the reaction.

23. The method as set forth in claim 21 wherein the film is wet by at least one of immersion or spraying and the film is wiped over the surface.

24. The method as set forth in claim 23 wherein the persalt and acetyl donor generate oxidant which breaks down into oxygen, the reaction being completed and the oxidant breaking down into oxygen in less than an hour.

25. A method of using the film of claim 2, the method comprising:
wetting the film with the dilutant such that the reaction between the perborate and the dry reagent progresses releasing oxygen;
controlling a rate at which oxygen is released by controlling pH of the solution; and
bringing the film into contact with a surface to be treated.

26. The method as set forth in claim 25 wherein:
the dry reagent is acetylsalicylic acid; and
a dry pH buffer controls the pH of the solution, such that the dilutant causes a reaction in which peracetic acid is generated in situ, adjusting the dry pH buffer adjusts the rate of reaction and stability of the peracetic acid such that the reaction and resultant peracetic acid is held nearer a neutral pH achieves a relatively long half-life and increasing the pH shortens the reaction time and half-life of the peracetic acid.

27. The method as set forth in claim 26 further including maintaining the dry acetylsalicylic acid and the dry perborate separated by one of:
separately encapsulating the dry acetylsalicylic acid and the dry perborate;
disposing the particles of the acetylsalicylic acid on one side of a filter material and disposing particles of the dry perborate on an opposite side of the filter material, the filter material having pores smaller than a physical size of the particles of the acetylsalicylic acid and the perborate;
adhering the dry acetylsalicylic acid to a first flexible layer and adhering the dry perborate to a second flexible layer, disposing the first and second flexible layers on opposite sides of the flexible, porous material; and,
impregnating particles of the acetylsalicylic acid and the perborate in the flexible, porous material in a physically displaced relationship to each other.

28. The method as set forth in claim 26 wherein the rate of reaction is adjusted such that the peracetic acid has a half-life of less than 10 minutes and further including wetting the flexible, porous material with a sufficient amount of water dilutant that as the flexible, porous material is wiped along a surface, a film of the peracetic acid solution is left on the surface.

29. The method as set forth in claim 26 wherein in the adjusting step, the pH is adjusted such that the peracetic acid breaks down to free oxygen and further including affixing the flexible, porous material to an injured surface of a patient such that the released free oxygen contacts the injured portion and promotes healing.

* * * * *